US011622920B2

(12) United States Patent
Schmaus et al.

(10) Patent No.: US 11,622,920 B2
(45) Date of Patent: Apr. 11, 2023

(54) DELIVERY SYSTEM FOR ACTIVE AGENTS

(71) Applicant: Symrise AG, Holzminden (DE)

(72) Inventors: Gerhard Schmaus, Höxter (DE); Sabine Lange, Holzminden (DE); Ann Christin Weseloh, Polle (DE); Dominik Stuhlmann, Holzminden (DE)

(73) Assignee: Symrise AG, Holzminden (DE)

( * ) Notice: Subject to any disclaimer, the term of this patent is extended or adjusted under 35 U.S.C. 154(b) by 585 days.

(21) Appl. No.: 15/778,693

(22) PCT Filed: Dec. 3, 2015

(86) PCT No.: PCT/EP2015/078598
§ 371 (c)(1),
(2) Date: May 24, 2018

(87) PCT Pub. No.: WO2017/092818
PCT Pub. Date: Jun. 8, 2017

(65) Prior Publication Data
US 2018/0353392 A1 Dec. 13, 2018

(51) Int. Cl.
A61K 8/02 (2006.01)
A61Q 19/00 (2006.01)
A61K 8/06 (2006.01)
A61K 8/60 (2006.01)
A61K 8/64 (2006.01)
A61K 8/73 (2006.01)
A61Q 19/02 (2006.01)
A61Q 19/06 (2006.01)
A61Q 19/08 (2006.01)
A61K 8/34 (2006.01)
A61K 8/37 (2006.01)
A61Q 19/04 (2006.01)
A61K 8/9783 (2017.01)
A61K 8/35 (2006.01)
A61K 8/49 (2006.01)
A61K 8/65 (2006.01)

(52) U.S. Cl.
CPC .......... A61K 8/0208 (2013.01); A61K 8/0212 (2013.01); A61K 8/062 (2013.01); A61K 8/345 (2013.01); A61K 8/347 (2013.01); A61K 8/35 (2013.01); A61K 8/375 (2013.01); A61K 8/4973 (2013.01); A61K 8/60 (2013.01); A61K 8/64 (2013.01); A61K 8/645 (2013.01); A61K 8/65 (2013.01); A61K 8/73 (2013.01); A61K 8/731 (2013.01); A61K 8/733 (2013.01); A61K 8/9783 (2017.08); A61Q 19/00 (2013.01); A61Q 19/005 (2013.01); A61Q 19/008 (2013.01); A61Q 19/02 (2013.01); A61Q 19/04 (2013.01); A61Q 19/06 (2013.01); A61Q 19/08 (2013.01); A61K 2800/434 (2013.01); A61K 2800/522 (2013.01); A61K 2800/524 (2013.01); A61K 2800/74 (2013.01)

(58) Field of Classification Search
None
See application file for complete search history.

(56) References Cited

U.S. PATENT DOCUMENTS

| | | | | |
|---|---|---|---|---|
| 4,070,496 A | * | 1/1978 | Rowsell | A24B 15/30 424/45 |
| 4,559,157 A | | 12/1985 | Smith et al. | |
| 5,141,803 A | * | 8/1992 | Pregozen | A61K 8/0208 15/104.93 |
| 6,458,379 B1 | | 10/2002 | Konno et al. | |
| 8,344,025 B2 | * | 1/2013 | Surburg | A23G 3/36 514/529 |
| 2003/0044599 A1 | * | 3/2003 | Sugii | C09J 7/381 428/343 |
| 2004/0048771 A1 | * | 3/2004 | McDermott | A61K 8/42 512/1 |
| 2004/0131660 A1 | | 7/2004 | Lange et al. | |
| 2006/0121099 A1 | | 6/2006 | Solarek | |
| 2006/0292244 A1 | * | 12/2006 | Reimer | A61K 9/127 424/617 |
| 2007/0166337 A1 | * | 7/2007 | Treudler | A61P 17/10 514/159 |
| 2007/0224231 A1 | | 9/2007 | Schmidt | |
| 2007/0248633 A1 | * | 10/2007 | Baldo | A61K 8/14 424/401 |
| 2009/0041687 A1 | * | 2/2009 | Beumer | A61K 31/485 514/315 |
| 2010/0260695 A1 | * | 10/2010 | Burke-Colvin | A61P 19/00 424/62 |

FOREIGN PATENT DOCUMENTS

FR 2830197 A1 4/2003
WO WO9921532 * 5/1999

* cited by examiner

Primary Examiner — Jennifer A Berrios
(74) Attorney, Agent, or Firm — Dilworth & Barrese, LLP

(57) ABSTRACT

The present invention belongs to the area of cosmetics, especially to a delivery system for actives to the skin, such as face masks and facial masks. Particularly, the present invention refers to a delivery system consisting of a basic body comprises nonwoven fibrous materials and an active-substance preparation which is an o/w emulsion or w/o emulsion, and a wetting liquid that comprises one or more actives to activate the delivery system.

15 Claims, No Drawings

DELIVERY SYSTEM FOR ACTIVE AGENTS

FIELD OF INVENTION

The present invention belongs to the area of cosmetics, especially to a delivery system for actives to the skin, such as face masks and facial sheet masks. Particularly, the present invention refers to a delivery system consisting of a basic body comprises non-woven fibrous materials and an active-substance preparation which is an o/w emulsion, and a wetting liquid that comprises one or more actives to activate the delivery system.

STATE OF THE ART

A series of known active compound release systems for skin exists, such as, for example, gels, ointments, creams, face masks, ampoules or plasters and the like. Within those delivery systems absorption of active compounds through the skin often depends on the base and the properties of the active compounds.

In any case, face masks and facial sheet masks are a growing category worldwide as delivery systems for actives to the skin. They are becoming increasingly popular, because they are one of the quickest ways to bring actives in contact with the skin.

However, the texture of face masks and the efficacy of the delivery of actives in known release systems are often not satisfying. Sometimes face masks of the prior art show stickiness and greasyness, and thus are uncomfortable. Another challenge is the difficulty of bringing the preparation that comprises the active agents onto the face mask material, which are e.g. cotton, linen or non woven tissues and the like.

The common way to equip the face masks material with actives is to soak the known "ready to use" face masks with a surplus of emulsion, containing the active ingredients. The disadvantages resulting from the soak are e.g. that the face masks make the application on the face a discomfortable, greasy issue.

The object of the invention was therefore to identify a suitable delivery system for actives onto skin without the aforementioned disadvantages. In particular, it was an object of the present invention to provide a preparation which could be applied onto a non-woven fabric to obtain a suitable release system. Specifically, such a preparation should be able to be printed onto a surface of the non-woven fabric. A further object was to provide a delivery system which shows sufficient liberation of the active ingredients to the skin and at the same time ensure an optimum efficacy within the application time. Furthermore, the delivery system of the present invention should be stable and the skin feel should be improved and thus less greasy feel occurs when applying to the consumers, especially in regard of face masks.

DESCRIPTION OF THE INVENTION

The present invention relates to a delivery system consisting of
(i) a basic body,
(ii) an active-substance preparation, and
(iii) a separate wetting liquid,
wherein the basic body consists of non-woven fibrous materials and the active-substance preparation is an o/w emulsion or w/o emulsion which is printed onto the basic body (i) and the wetting liquid (iii) comprises one or more actives to start the liberation of the actives of the active-substance preparation.

Surprisingly, it has been discovered that the delivery system of the present invention advantageously improve the liberation of actives to the skin and the skin feel versus delivery system in which the basic body is soaked with active-substance preparation.

Preferably, a suitable basic body for the present invention is a sheet-like structure comprising a main part that consists of a textile material and having fibers, thus active substances could be printed onto the surface of the basic body. Such a basic body is for instance described in DE 102014003731 A1 (FREUDENBERG).

Suitable fibrous materials are preferably selected from natural or synthetic fibrous material and combination thereof. Natural fibers are preferably textile fibers and fiber materials which are obtained without chemical modification of plant and animal materials. Preferably, plant fibers are a collective term for fibers of vegetable origin, which are used as materials such as seeds fibers, bast fibers and masonite fibers e.g. cotton fibers, bamboo fibers, coconut fiber and a mixture thereof. The choice of fibers depends upon, for example, fiber cost and the desired properties, e.g., liquid resistance, vapor permeability or liquid wicking of the finished product, wherein face masks are in particular preferred. For example, suitable fibrous materials may include, but are not limited to, synthetic fibers such as those derived from polyolefins, polyesters, polyamides, polyacrylics, etc., alone or in combination with one another. Similarly, natural fibers such as cotton, linen, jute, hemp, cotton, wool, wood pulp, etc.; regenerated cellulosic fibers such as viscose rayon and cuprammonium rayon; or modified cellulosic fibers, such as cellulose acetate may likewise be used. Blends of one or more of the above fibers may also be used if so desired.

In a preferred embodiment the o/w emulsion of the active-substance preparation of the present delivery system comprises
(a) one or more active agents selected from the group consisting of whitening or brightening agents, skin cell renewal agents, anti-ageing agents, deodorant actives, anti cellulite agents, moisturizing agents, actives for sensitive skin, actives for the treatment of oily skin, antimicrobials, anti-acne drugs, antiperspirant compounds, antihistamines, anti-inflammatory agents, skin protective agents, insect repellent chemicals, sunscreens, fragrances, preservatives, actives for hair coloration, solvents or a mixture thereof, and
(b) a carrier selected from the group consisting of sugars such as sucrose, glucose, lactose, levulose, trehalose, fructose, maltose, ribose, dextrose, isomalt, sorbitol, mannitol, xylitol, lactitol, maltitol, pentatol, arabinose, pentose, xylose, galactose; hydrogenated starch hydrolysates, inulin, and polysaccharides such as oligofructose; maltodextrins or dextrins (soluble fiber); hydrocolloids such as agar, gum acacia, modified gum acacia, sodium alginate, potassium alginate, ammonium alginate, calcium alginate or carrageenan; gums; polydextrose; celluloses such as sodium carboxymethylcellulose, enzymatically hydrolyzed carboxy methyl cellulose, methyl cellulose, hydroxypropyl cellulose and hydroxypropyl methyl cellulose; triglycerides such as medium-chain triglycerides (MCT) whose fatty acids have an aliphatic tail of 6-12 carbon atoms, and long-chain triglycerides (LCT) whose fatty acids have an aliphatic tail of 14-24 carbon atoms;

proteins such as gelatin, pea protein, soy and whey protein isolates and hydrolyzates, and sodium caseinates or a mixture thereof.

The combination of said active agents with a carrier in an o/w emulsion or w/o emulsion is advantageously for the incorporation of the actives in the emulsion to the polymer matrix of the basic body, when applying the emulsion onto the basic body to obtain the delivery system. The emulsion, containing active ingredients will form matrix particles during the drying process. The active ingredients of the emulsion are embedded in the matrix particles in such a way that the active agents are well protected and kept from degradation, in particular because of external environmental conditions.

In a preferred embodiment of the present delivery system is an o/w emulsion of the active-substance preparation and comprises at least one or more polysaccharides as carrier material, which is preferably selected from the group consisting of maltodextrin, modified starch, dextrin, gummi *arabicum*, mannitol, cellulose derivatives or a mixture thereof.

It has been observed that delivery systems, which comprises an o/w emulsion containing polysaccharides as the active-substance preparation improves significantly the delivery of an active ingredient versus emulsion without polysaccharides.

The delivery system of the present invention is a two component system, and thus is advantageous for that the active ingredients are well protected before activation. Actives with reduced stability in water could be as well incorporated into the present delivery system due to the use of a two component system. Further, different actives could be combined which are usually not compatible with each other in long term stability.

In another preferred embodiment the active-substance preparation (ii) of the delivery system of the present invention is an o/w emulsion that comprise
(a) from 0.001 w.t. % to 70 w.t. % of one or more active agents, preferably from 0.01 w.t % to 50 w.t. %, more preferably from 0.1 w.t. % to 40 w.t. % and
(b) from 5 w.t. % to 50 w.t. %, preferably 10 w.t. % to 40 w.t. %, more preferably 15 w.t. % to 30 w.t. %, most preferred 15 w.t. % to 25 w.t. % of a carrier material, each based on the total amount of the active-substance preparation.

More preferably the amount of the carrier materials is at least 10 w.t %, more preferably at least 15 w.t. % referring to the total amount of the active-substance preparation.

The carrier material is preferably maltodextrin or a mixture of maltodextrin with a further suitable carrier material as described herein. In particular preferred is the use of 12% w.t. to 20% w.t. of maltodextrin or a mixture of maltodextrin with a further suitable carrier material, e.g. with modified starch, dextrin, gummi *arabicum*, mannitol or cellulose derivatives.

It has been discovered that within the said ranges of active agents and carrier, preferably maltodextrin in an emulsion to be applied onto a basic body that consists of nonwoven fibrous materials the emulsion could be printed or sprayed onto said basic body. The technology is a dot printing process, which is well known and prior art: The non woven is fixed on a dry and even surface; a perforated metal plate is fixed on the top. The emulsion is then applied on the upper side and spread by a metal bar. Then the samples are dried at 70-90° C. The treated surface shows good quality of the delivery system, especially in aspects of the stability and liberation of the active agents as well as a soft skin feel and grip. Particular preference is made to non-woven fibrous materials as described herein.

In a further embodiment, the delivery system of the present invention is a cosmetical or pharmaceutical care system for skin; preferably face masks, facial sheet masks, treatments for upper legs and arms, arm pits, breast or back.

Preferably, the delivery system of the present invention have a two or three dimensional structure of a face of a necklines, a hand, an arm, a foot, a leg or other parts of the body or adapts to the structure of parts of the body.

The non-woven fibrous material of the present invention could be configured as a non-woven or non-woven fabric. This is advantageous because a particularly flat construction can be realized and the basic body may be elastic. This allows a wearing comfort of the delivery system of the present invention. Preferably, a non-woven fabric is used for the present invention. Such a non-woven fabric could also be mechanically, chemically and/or thermally consolidated for the intention used of the present invention.

Sheet-Like Cosmetic Delivery Agent

A further object of the invention is a sheet-like cosmetic delivery system which is obtainable by printing, spraying and impregnating non-woven fibrous materials with an o/w emulsion or w/o emulsion of an active-substance preparation comprising
(a) at least one active agent in an amount from 0.001 w.t. % to 70 w.t. % preferably from 0.01 w.t % to 50 w.t. %, more preferably from 0.1 w.t. % to 40 w.t. %, and
(b) carrier material in an amount from 5 w.t. % to 50 w.t. %, preferably 10 w.t. % to 40 w.t. %, more preferably 15 w.t. % to 30 w.t. %, most preferred 15 w.t. % to 25 w.t. %, each based on the total amount of the active-substance preparation, wherein the active agent a) is printed onto the matrix of the basic body which consists of non-woven fibrous materials. Preferably the carrier material comprises at least maltodextrin. Particular preference is made to o/w emulsion.

The cosmetic delivery system of the present invention is preferably a face mask or a sheet mask for the face or other areas of the body.

It has been observed that the delivery system of the present invention is in particular advantageously for the use of the release of a series of active agents for that the delivery system of the present invention shows a good liberation rate of active agents once the delivery system is activated. Furthermore the greasy skin feel could be reduced compared to a ready to use face mask soaked with emulsion instead of printing.

Thus, another aspect of the present invention is the use of the delivery system of the present as described herein for the liberation of cosmetic al or pharmaceutical active agents to the (human) skin, in particular of active agents such as e.g. whitening or brightening agents, skin cell renewal agents, anti-ageing agents, deodorant actives, anti cellulite agents, moisturizing agents, actives for sensitive skin, actives for the treatment of oily skin, antimicrobials, anti-acne drugs, antiperspirant compounds, antihistamines, anti-inflammatory agents, skin protective agents, insect repellent chemicals, sunscreens, fragrances, preservatives, actives for hair coloration, solvents and mixtures thereof. The active agents are described in detail below.

In a preferred embodiment of the use of the present invention the delivery system is a face mask or facial sheet mask.

Emulsions

A further important aspect of the invention is the active-substance preparation emulsion, comprising (a) from 0.001 w.t. % to 70 w.t. % preferably from 0.01 w.t % to 50 w.t. %, more preferably from 0.1 w.t. % to 40 w.t. %, of one or more active agents, and
(b) from 5 w.t. % to 50 w.t. %, preferably 10 w.t. % to 40 w.t. %, more preferably 15 w.t. % to 30 w.t. %, most preferred 15 w.t. % to 25 w.t. % of a carrier material, which preferably comprises at least maltodextrin.

Furthermore an object of the invention is the use of said emulsion for printing onto suitable surfaces like the non-woven fibrous material as described herein. More preferably the amount of the carrier materials is at least 10 w.t %, more preferably at least 15 w.t. % referring to the total amount of the active-substance preparation. Surprisingly, it has been observed that an o/w emulsion with such ranges of active agents and carrier, preferably maltodextrin in an emulsion, show a good adhesion onto non-woven fibrous materials as described herein and a good material quality after drying. Further, a good release and liberation of active agents as well as a good feel comfort during the application of the delivery system could be observed.

Method of Delivering Active Agents

A further object of the present invention is a method of delivering active agents to the skin, comprising the steps of:
(i) providing a basic body that consists of non-woven fibrous materials on which an active-substance preparation is printed to in such a way that the active agents are embedded into the matrix of the basic body, to the part of the skin which is to be treated with active agents,
(ii) bringing the basic body resulting from step (i) in contact of a wetting liquid, which comprises one or more actives to start the liberation of actives of the active-substance preparation, with to release the active agents to the skin part which is to be treated with.

Preferably the active agent of the active-substance preparation to be released is a whitening or brightening agent, preferably selected from skin whitening agent or hair brightening agent (bleaching products), most preferably the whitening or brightening agent of the present invention is a skin whitening agent, e.g. selected from diphenylmethanes, which have been described in US 2007/0098655, macrocyclic compounds as described in U.S. Pat. No. 6,759,557 or any botanical extracts that contain components that inhibit melanin production in skin such as sclareolide; *Tetraselmis Suecica* Extract; licorice extract; pomegranate extract; hinokitiol; protocatechuic acid; NAB asafetida (*Ferula Foetida*) extract; resveratrol and his derivatives such as oxyresveratrol, resveratrol, resveratrol phosphate, resveratrol ferulate; ferulic acid and its derivatives such as ferulic acid phosphate; viniferol; botanical extract combinations sold by Coletica under the Phytoclar® (Saxifrage, Grape, mulberry and *Scutelleria* Root extracts), Phytowhite® (cucumber, apple and Scutellaria extracts) or Phytolight® (cucumber, apple and Scutellaria, and green tea extracts); Lunawhite B° (butylene glycol/water/*Denothera Biennis* seed extract) evening primrose extract; fatty acid esters of ascorbic acid such as ascorbyl palmitate; *Euphrasia Officianalis* extract, purine derivatives such as kinetin or derivatives thereof; ascorbyl glucoside; grape seed extract; vineferol, pomegranate extract, tetrahydrocurcumins, *Acmella Oleracea* extract, Aloesin, Tyrostat®, which are extracts of field dock, *aspergillus* ferment, molasses, 4-(1-Phenylethyl) 1-,3 benzenediol and combinations of these ingredients.

Preferably the whitening agent is 4-(1-Phenylethyl) 1-,3 benzenediol.

Preference is also given to delivery systems of the present invention that comprise one or more layers of fibrous materials. It is possible that the delivery system of the present invention consists of one layer. Nevertheless in principle it is possible that the basic body consists of at least one or more further layers. With more layers the stability of the basic body may be increased.

The raised number of layers can also have the advantage to charge different actives into different layers, thus to provide more control about the liberation of the active agents.

Maltodextrin

Maltodextrin is available in various qualities. A preferred maltodextrin, suitable as carrier material in the sense of the present invention possess the following specification:
Dextrose 0.1-10%, preferably 1-5%, more preferably 2-3%;
Maltose 0.1-10%, preferably 2-9%, more preferably 5-7%;
Triose 0.1-15%, preferably 5-13%, more preferably 7-10%;
Higher Polysaccharides: 70-95%, preferably 70-90%, more preferably 75-82%

The active-substance preparation emulsion of the present invention may comprise further ingredients which are usually used in the cosmetic or pharmaceutical areas.

Pharmaceutical compositions according to the present invention may include similar additives as for the cosmetic application, such as for example oil bodies or emulsifiers etc. It should also be mentioned that several actives cited in the following can also be incorporated in cosmetic formulations and vice versa in pharmaceutical formulations. Therefore, the border between cosmetic and pharmaceutical compositions is in flow and it should be understood that components cited for one application are recommended for the other mutatis-mutandis without literal repetition.

Preferably for the use in cosmetic or pharmaceutical area active-substance preparation emulsions of the present invention may further contain ingredients selected from abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxyl acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

The active agents of the active-substance preparation and the further cosmetically acceptable ingredients are described below in detail.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and di-alkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emuslifiers

Other surfactants may also be added as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grunau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4"-(1,3,5-triazine-2,4,6-triyl-triimino)tribenzoate (=2,4,6-trianilino-(p-carbo-2'-ethylhexyl-1'-oxy)-1,3,5-triazine) (Uvinul® T150).

Broadband filters which are preferably used in preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters which are preferably selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/ (Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilypoxy)disiloxanyl) propyl) (Mexoryl® XL)
4,4'-[(6-[4-(1,1-dimethyl)aminocarbonyl) phenylamino]-1,3,5-triazine-2,4-diyl)diimino]bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment the active-substance preparation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobic, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and *ramulus* species, extracts of pine species (*pinus*), extracts of *vitis* species or stilbene derivatives isolated or concentrated therefrom, saxifrage extract, *scutelleria* extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, *ginseng*, liquorice, honeysuckle, *sophora, pueraria, pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-aminon-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and

*lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shiake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), SynGlycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 Antagonists.

Suitable compounds which reduce the hypersensitivity of skin nerves based on their action as TRPV1 antagonists encompass e.g. trans-4-tert-butyl cyclohexanol as described in WO 2009 087242 A1, or indirect modulators of TRPV1 by an activation of the µ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations including actives according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-betacitronellol, panthenol, glycogen for example from mussels, extracts from microorganisms, algae, plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, *Isochrysis galbana*, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gammaglutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Cooling Agents

Formulations including actives according to the present invention may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, I-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, monomenthylglutarate, mono-menthylmalonate, O-menthyl succinic acid ester-N,N(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl) amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(–)-isopulegol, I-(–)isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl) ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, and alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, -isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Natural perfumes and fragrances possible as actives for the present delivery system include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used.

Typically, the synthetic fragrances represent aldehydes, ketones, alcohols, ethers, esters, hydrocarbons their mixtures. In the following these types of fragrances are illustrated but not limited by examples:

Aldehydes.

Examples for suitable fragrances showing an aldehyde structure encompass melonal, triplal, ligustral, adoxal, anisaldehyde, cymal, ethylvanillin, florhydral, floralozon, helional, heliotropin, hydroxycitronellal, koavon, laurinaldehyde, canthoxal, lyral, lilial, adoxal, anisaldehyde, cumal, methyl-nonyl-acetaldehyde, citronellal, citronellyloxyacetaldehyde, cyclamenaldehyde, bourgeonal, p-tert.-bucinal, phenylacetaldehyde, undecylenaldehyde, vanillin; 2,6,10-trimethyl-9-undecenal, 3-dodecen-1-al, α-nAmylzimtaldehyde, 4-methoxy-benz-aldehyde, benzaldehyde, 3-(4-tert-butylphenyl)propanal,2-methyl-3-(para-methoxy-phenylpropanal), 2-methyl-4-(2,6,6-trimethyl-2(1)cyclohexen-1-yl)butanal,3-phenyl-2-pro-penal, cis-/trans-3,7-dimethyl-2,6-octadien-1-al, 3,7-dimethyl-6-octen-1-al,[(3,7-dimethyl-6-octenyl)-xy]-cetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxyaldehyde, 2-methyl-3-(isopropyl-phenyl)propanal, decyl aldehyde, 2,6-dimethyl-5-heptenal; 4-(tricyclo[5.2.1.0 (2,6)]-decylidene-8)-butanal; octahydro-4,7-methano-IH-indenecarboxaldehyde; 3-ethoxy-4-hydroxybenzaldehyde, para-ethyl-alpha,alpha-dimethylhydrozimtaldehyde, α-methyl-3,4-(methylenedioxy)-hydrocinnamaldehyde, 3,4-methylendioxybenzaldehyde, α-n-hexyl-cinnamaldehyde, m-cymene-7-carboxaldehyde, α-methylphenylacetaldehyde, 7-hydroxy-3,7-dimethyl octanal, undecenal, 2,4,6-trimethyl-3-cyclohexene-1-carboxalde-hyde, 4-(3)(4-methyl-3-pentenyl)-3-cyclohexen-carboxaldehyde, 1-dodecanal, 2,4-dimethyl-cyclohexene-3-carboxaldehyde, 4-(4-hydroxy-4-methylpentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, 3-(4-ethylphenyl)-2,2-dimethylpropanal, 3-(4-methoxyphenyl)-2-methylpropanal, methylno-nylacetaldehyde, 2-phenylpropan-1-al, 3-phenylprop-2-en-1-al, 3-phenyl-2-pentyl-prop-2-en-1-al, 3-phenyl-2-hexylprop-2-enal, 3-(4-isopropylphenyl)-2-methylpropan-1-al, 3-(4-ethyl phenyl)-2,2-di methylpropan-1-al, 3-(4-tert-butylphenyl)-2-methylpropanal, 3-(3,4-Methylendioxy-phenyl)-2-methylpropan-1-al, 3-(4-Ethylphenyl)-2,2-dimethylpropanal, 3-(3-Isopropylphenyl)-butan-1-al, 2,6-Dimethylhept-5-en-1-al, Dihydrozimtaldehyde, 1-methyl-4-(4-methyl-3-pentenyl)-3-cyclohexene-1-carboxaldehyde, 5- or 6-Methoxyhexahydro-4,7-methanoindan-1 or 2-carboxyaldehyde, 3,7-dimethyloctan-1-al, 1-undecanal, 10-undecen-1-al, 4-hydroxy-3-methoxybenzaldehyde, 1-methyl-3-(4-methyl pentyl)-3-cyclohexene-carboxyaldehyde, 7-hydroxy-3,7-dimethyloctanal; trans-4-decenal, 2,6-nonadienal, p-tolylacetaldehyde; 4-methylphenylacetaldehyde, 2-methyl-4-(2,6,6-trimethyl-1-cyclohexen-1-yl)-2-butenal, omethoxyzimtaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindan-1-carboxaldehyde, octanal, 2-methyl octanal, alpha-methyl-4-(1-methylethyl)benzeneacetaldehyde, 6,6-dimethyl-2-norpinene-2-propionaldehyde, p-methyl phenoxy acetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, 1-p-menthene-q-carboxaldehyde, citral or its mixtures, lilial citral, 1-decanal, n-undecanal, n-dodecanal, hlorhydral, 2,4-dimethyl-3-cyclohexen-1-carboxaldehyde 4-methoxybenzaldehyde, 3-methoxy-4-hydroxy-benzaldehyde, 3-ethoxy-4-hydroxybenzaldehyde, 3,4-methylendioxybenzaldehyde, 3,4-dimethoxybenzaldehyde and their mixtures.

As explained above, said ketones or said aldehydes may show an aliphatic, cycloaliphatic, aromatic, ethylenically unsaturated structure or a mixture of these elements. The components may also include heteroatoms or show a polycyclic structure. Suitable substituents for all these structures are hydroxyl and/or amino groups. Further fragrances are compiled in the following document: Steffen Arctander "Published 1960 and 1969 respectively, Reprinted2000 ISBN: Aroma Chemicals Vol. 1: 0-931710-37-5, Aroma Chemicals Vol. 2: 0-931710-38-3", which is hereby incorporated by reference.

Ketones.

Examples for suitable fragrances showing a ketone structure encompass buccoxime, iso jasmone, methyl beta naphthyl ketone, moschus indanone, tonalid/moschus plus, α-damascone, β-damascon, δ-damascone, Iso-damascone, damascenone, damarose, methyl-dihydrojasmonate, menthone, carvone, campher, fenchone, alphalonen, β-iononw, dihydro-β-Ionone, γ-methylionone, fleuramone, dihydrojasmone, cis-Jasmon, iso-E-Super, methyl cedrenylk etone, or methyl cedrylon, acetophenone, methyl aceto phenone, p-methoxyacetophenone, methyl-(3-naphtyl ketone, benzylacetone, benzophenone, p-hydroxy phenylbutanone, celery Ketone or livescon, 6-osopropyl-deca-hydro-2-naphtone, dimethyloctenone, freskomenth, 4-(1-ethoxyvinyl)-3,3,5,5,-tetramethylv cyclohexanone, methylheptenone, 2-(2-(4-Methyl-3-cyclohexen-1-yl)propyl)-cyclopentanone, 1-(p-menthene-6(2)-yl)-1-propanone, 4-(4-Hydroxy-3-methoxyphenyl)-2-buta none, 2-Acetyl-3,3-dimethyl-norbornan, 6,7-dihydro-1,1,2,3,3-pentamethyl-4(5H)-indanone, 4-damascol, dulcinyl or cassione, gelsone, hexalone, isocyclemone E, Methylcyclocitrone, methyl lavender ketone, orivone, p-tert-butyl cyclohexanone, verdone, delphone, muscone, neobutenone, plicatone, veloutone, 2,4,4,7-tetramethyl-oct-6-en-3-one, tetrameran, hedion and their mixtures. The preferred ketones are selected from the group comprising α-damascone, δ-damascone, iso-damascone, carvone, γ-methyl ionone, Iso-E-Super, 2,4,4,7-tetramethyl-oct-6-en-3-one, benzylacetone, β-damascone, damascenone, methyl dihydrojasmonate, methyl cedrylone, hedione and their mixtures Alcohols.

Suitable fragrance alcohols encompass for example 10-undecen-1-ol, 2,6-dimethylheptan-2-ol, 2-methylbutanol, 2-methylpentanol,2-phenoxyethanol, 2-phenylpropanol, 2-tert-Butycyclohexanol, 3,5,5-trimethylcyclohexanol, 3-hexanol, 3-methyl-5-phenylpentanol, 3-octanol, 1-octen-3-ol, 3-phenylpropanol,4-heptenol, 4-isopropylcyclohexanol, 4-tert-butylcyclohexanol, 6,8-dimethyl-2-nonanol,6-nonen-1-ol, 9-decen-1-ol, α-methyl benzylalcohol, α-terpineol, amylsalicylat, benzyl alcohol, benzyl salicylate, β-terpineol, butyl salicylate, citronellol, cyclohexyl salicylate, decanol, dihydromyrcenol, dimethyl benzylcarbinol, dimethyl heptanol, dimethyl octanol, ethyl salicylate, ethyl vanilin, anethol, eugenol, geraniol, heptanol, hexyl salicylat, isoborneol, isoeugenol, isopulegol, linaloof, menthol, myrtenol, n-hexanol, nerol, nonanol, octanol, para-menthan-7-ol, phenylethylalkohol, phenol, phenyl salicylat, tetrahydro geraniol, tetrahydro linalool, thymol, trans-2-cis-6-nonadienol, trans-2-nonen-1-ol, trans-2-octenol, undecanol, vanillin, cinnamalcohol and their mixtures.

Esters.

Examples for suitable fragrances showing a ketone structure encompass benzyl acetate, phenoxyisobutyrate, p-tert.-butylcyclohexylacetate, linalylacetate, dimethylbenzylcarbinylacetate (DMBCA), phenylethylacetate, benzylacetate, ethylmethylphenylglycinate, allylcyclohexylpropionate, styrallylpropionate, benzylsalicylate, cyclohexylsalicylate, floramat, melusat, jasmacyclatat and their mixtures.

Ethers.

Examples for suitable fragrances showing a ketone structure encompass benzylethyl ether or ambroxan Hydrocarbons.

Examples for suitable fragrances representing hydrocarbons encompass terpenes, e.g. limonen and pinen.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3Fe_3O_4$, FeO (OH)) and/or tin oxide. Advantageous dyes are for example carmine, Berlin blue, chromium oxide green, ultramarine blue and/or manganese violet.

Anti-Irritation Agents

An important group of co-actives encompass anti-irritant agents such as for example steroidal anti-inflammatory substances of the corticosteroid type, such as e.g. hydrocortisone, hydrocortisone derivatives, such as hydrocortisone 17-butyrate, dexamethasone, dexamethasone phosphate, methylprednisolone or cortisone; non-steroidal anti-inflammatories like oxicams, such as piroxicam or tenoxicam; salicylates, such as aspirin, Disalcid, Solprin or fendosal; acetic acid derivatives, such as diclofenac, fenclofenac, indomethacin, sulindac, tolmetin or clindanac; fenamates, such as mefenamic, meclofenamic, flufenamic or niflumic; propionic acid derivatives, such as ibuprofen, naproxen or benoxaprofen, or pyrazoles, such as phenylbutazone, oxyphenylbutazone, febrazone or azapropazone. Alternatively, natural anti-inflammatory substances or reddening- and/or itching-alleviating substances can be employed. Plant extracts, specific highly active plant extract fractions and highly pure active substances isolated from plant extracts, can be employed like extracts, fractions and active substances from aloe vera, *Commiphora* species, *Rubia* species, *Rubus* species, willow, rose-bay, willowherb, oats, calendula, *arnica*, St. John's wort, honeysuckle, ginger, chamomile, rosemary, sage, melissa, *Passiflora incarnata*, Sophora *japonica*, witch hazel, *Pueraria, Dianthus* or *Echinacea*, as well as pure substances, such as, inter alia, bisabolol, apigenin, apigenin-7-glucoside, rosmarinic acid, boswellic acid, phytosterols, glycyrrhizic acid, glabridin, licochalcone A, [6]-paradol, and anthranilic acid amides, such as, in particular, avenanthramides or dianthramides, are particularly preferred. The total amount of anti-irritants in a formulation or product according to the invention is preferably in the range of from 0.0001 to 20 wt. %, preferably from 0.0001 to 10 wt. %, in particular from 0.001 to 5 wt. %, based on the total weight of the formulation or product, respectively.

Particular useful co-actives are selected from the group consisting of anti-mycotica and pain relief agents, and more particularly the group consisting of erythromycin, dimetindene, betamethasone, ibuprofen, ketoprofene, diclofenac, metronidazole, acyclovir, imiquimod, terbinafine, docosanol, cyclopyroxolamine, and their mixtures:

Erythromycin is a macrolide antibiotic that has an antimicrobial spectrum similar to or slightly wider than that of penicillin, and is often used for people who have an allergy to penicillin.

Dimetindene, also known as Fenistil (RS-dimethyl(2-(3-[pyridin-2-yl)ethyl]-1H-inden-2-yl)ethyl)amine) is an antihistamine/anticholinergic used orally and locally as an antipruritic.

Betamethasone (8S,9R,10S.11S,13S,14S,16S,17R)-9-fluoro-11,17-(2-hydroxyacetyl)-10, 13,16-trimethyl-6,7,8,9, 10,11,12,13,14,15,16,17-dodecahydro-3H-cyclopenta(alpha)phenanthren-3-one) is a potent glucocorticoid steroid with anti-inflammatory and immunosuppressive properties.

Ibuprofen (RS)-2-(4-(2-methylpropyl)phenyl)propanoic acid) from the nomenclature iso-butyl-propanoic-phenolic acid) is a non-steroidal anti-inflammatory drug (NSAID) used for relief of symptoms of arthritis, fever, as an analgesic (pain reliever), especially where there is an inflammatory component, and dysmenorrhea.

Ibuprofen is known to have an antiplatelet effect, though it is relatively mild and somewhat short-lived when compared with aspirin or other better-known antiplatelet drugs. In general, ibuprofen also acts as a vasoconstrictor, having been shown to constrict coronary arteries and some other blood vessels mainly because it inhibits the vasodilat-ing prostacyclin produced by cyclooxygenase 2 enzymes. Ibuprofen was derived from propanoic acid by the research arm of Boots Group during the 1960s and was patented in 1961. Originally marketed as Brufen, ibuprofen is available under a variety of popular trademarks, including Motrin, Nurofen, Advil, and Nuprin (see U.S. Pat. No. 3,385,886 Boots).

Ketoprofen (RS)2-(3-benzoylphenyl)-propionic acid is another one of the propionic acid class of non-steroidal anti-inflammatory drug (NSAID) with analgesic and antipyretic effects.

It acts by inhibiting the body's production of prostaglandins (see U.S. Pat. No. 3,641,127—Rhone-Poulenc).

Diclofenac is also a non-steroidal anti-inflammatory drug (NSAID) taken to reduce inflammation and as an analgesic reducing pain in certain conditions.

Metronidazole (2-(2-methyl-5-nitro-1H-imidazol-1-yl) ethanol) is a nitroimidazole antibiotic medication used particularly for anaerobic bacteria and protozoa.

Terbinafine, more particularly terbinafine hydrochloride [(2E)-6,6-dimethylhept-2-en-4-yn-1-yl](methyl)(naphthalen-1-ylmethyl)amine) is a synthetic allylamine antifungal from Novartis. It is highly lipophilic in nature and tends to accumulate in skin, nails, and fatty tissues.

It is sold by the name Lamisil in Argentina, Australia, Belgium, Brazil, Canada, Chile, Egypt, Finland, France, Germany, Greece, Hungary, Iceland, Ireland, Israel, Mexico, Pakistan, Peru, New Zealand, Norway, Romania, Russia, Slovenia, South Africa, Sweden, United Kingdom, United States and Venezuela, also sold under the name Corbinal and Terbisil in Turkey and under the name "undofen cream" in Poland. As a generic it is sold under the name Zabel in Australia. It is also available as a generic medication in the United States, United Kingdom, Belgium, Switzerland and Brazil. In India, Terbinafine hydrochloride is available in topical form under the brand name Sebifin (Ranbaxy Labs), Zimig (GSK Pharma) and mycoCeaze (Progres Laboratories). MycoVa, developed by Apricus Biosciences, is a topical nail solution of terbinafine and DDAIP which has completed three Phase III studies for the treatment of onychomycosis (see U.S. Pat. No. 4,755,534—Sandoz).

Docosanol, also known as behenyl alcohol, is a saturated fatty alcohol used traditionally as an emollient, emulsifier, and thickener in cosmetics, nutritional supplement (as an individual entity and also as a constituent of policosanol), and more recently, in a Food and Drug Administration (FDA) approved pharmaceutical, Abreva, approved as an antiviral agent for reducing the duration of cold sores caused by the herpes simplex virus.

Ciclopiroxolamine (6-cyclohexyl-1-hydroxy-4-methylpyridin-2(1H)-one) also called Batrafen, Loprox, Mycoster, Penlac and Stieprox, is a synthetic antifungal agent for topical dermatologic treatment of superficial mycoses.

It is most useful against *Tinea versicolor* (see U.S. Pat. No. 3,883,545—Marck).

EXAMPLES

Example 1

Release Trials from Non-Woven Fabric

Three different formulation types have been prepared to evaluate the liberation of the active agent phenylethyl resorcinol from a non-woven fabric:

TABLE 1

Lipophilic mixture (formula 1)

| INCI | w/w % |
|---|---|
| Glyceryl oleate citrate/Caprylic/Capric triglyceride | 4.0 |
| Phenylethyl Resorcinol | 0.5 |
| Menthyl Ethylamido Oxalate | 1.0 |
| Caprylic/Capric/Triglycerides | 94.3 |
| Bisabolol, *Zingiber Officinale* (Ginger) Root Extract | 0.2 |
| Sum | 100.0 |

Production Method:

Blend all ingredients as listed.

TABLE 2

Polyvinylalcohol (PVOH) based emulsion (formula 2)

| INCI | w/w % |
|---|---|
| Polyvinyl Alcohol | 20.0 |
| Water (Aqua) | Ad 100 |
| Caprylic/Capric/Triglyceride | 17.3 |
| Hydroxyacetophenone | 0.5 |
| Phenylethylresorcinol | 0.5 |
| Menthyl Ethylamido Oxalate | 1.0 |
| Bisabolol, *Zingiber Officinale* (Ginger) Root Extract | 0.2 |
| Sum | 100.0 |
| pH value | 5.5 |

Production Method:

Disperse Polyvinyl Alcohol in cold water and heat the dispersion up to 85-90° C. Keep the temperature for about 1.5 h constant and then add all remaining ingredients as listed in table 2 and homogenize by using an Ultra Turrax Stirrer. Afterwards allow the mixture to cool down by using a vane stirrer.

TABLE 3 o/w emulsion with and without maltodextrin (formula 3 + 4) amounts is w/w %

| Phase | INCI | 3 | 4 | 5 | 6 |
|---|---|---|---|---|---|
| A. | Glyceryl Oleate Citrate | 1.5 | 1.5 | 1.5 | 1.5 |
| | Caprylic/Capric/Triglycerides | 10.0 | 10.0 | 10.0 | 10.0 |
| | Phenyletyl Resorcinol | 0.5 | 0.5 | 0.5 | 0.5 |
| | Tocopherol Acetate | 0.5 | 0.5 | 0.5 | 0.5 |
| | Menthyl Ethylamido Oxalate | 1.5 | 1.5 | 1.5 | 1.5 |
| | Bisabolol, *Zingiber Officinale* (Ginger) Root Extract | 0.2 | 0.2 | 0.2 | 0.2 |
| | Diethylhexyl Syringylidenemalonate, Caprylic/Capric Triglyceride | 0.1 | 0.1 | 0.1 | 0.1 |
| B. | Ammonium Acryloyldimethyltaurate/VP Copolymer | 1.0 | 1.0 | 1.0 | 1.0 |
| C. | Water (Aqua) | Ad 100 | Ad 100 | Ad 100 | Ad 100 |
| | Hydroxyacetophenone | 0.5 | 0.5 | 0.5 | 0.5 |
| | Maltodextrin | 15.0 | 0 | 5.0 | 45.0 |
| | Disodium EDTA | 0.1 | 0.1 | 0.1 | 0.1 |
| | Pentylene Glycol | 5.0 | 5.0 | 5.0 | 5.0 |
| | Citric Acid, 10% sol. | 0.2 | 0.2 | 0.2 | 0.2 |
| | Sum | 100.0 | 100.0 | 100.0 | 100.0 |
| | pH value | 4.8 | 4.8 | 4.8 | 4.8 |

Production Method:

Heat up phase A and C separately to approx. 80° C. Pre-disperse phase B in A by stirring (mixture AB). Add phase C to mixture AB and emulsify the mixture (2 min., Ultra Turrax Stirrer). Then reduce stirring speed while base is cooling (vane stirrer).

TABLE 4

Anti ageing o/w emulsions containing carnosine +/− maltodextrin; amounts in w/w %

| Phase | INCI | 7 | 8 | 9 | 10 |
|---|---|---|---|---|---|
| A. | Glyceryl Stearate Citrate | 2.0 | 2.0 | 2.0 | 2.0 |
| | Triisononanoin | 10.0 | 10.0 | 10.0 | 10.0 |
| | Caprylic/Capric/Triglycerides | 3.0 | 3.0 | 3.0 | 3.0 |
| | Tocopherol Acetate | 0.5 | 0.5 | 0.5 | 0.5 |
| | *Zingiber Officinale* (Ginger) Root Extract | 0.2 | 0.2 | 0.2 | 0.2 |
| B. | Xanthan Gum | 0.2 | 0.2 | 0.2 | 0.2 |
| C. | Water (Aqua) | Ad 100 | Ad 100 | Ad 100 | Ad 100 |
| | Carnosine | 0.2 | 0.2 | 0.2 | 0.2 |
| | Butylene Glycol, Pentylene Glycol, Hydroxyphenyl Propamidobenzoic Acid | 2.0 | 2.0 | 2.0 | 2.0 |
| | Hydroxyacetophenone | 0.8 | 0.8 | 0.8 | 0.8 |
| | Maltodextrin | 15.0 | | 25 | 5.0 |
| | Disodium EDTA | 0.1 | 0.1 | 0.1 | 0.1 |
| | Pentylene Glycol | 5.0 | 5.0 | 5.0 | 5.0 |
| | Sum | 100.0 | 100.0 | 100.0 | 100.0 |
| | pH value | 5.4 | 5.5 | 5.4 | 5.5 |

Production method:

see table 3

TABLE 5

Wetting liquid (formula A)

| INCI | w/w % |
|---|---|
| Glycerin, 86.5% | 30.0 |
| Pentylene Glycol | 5.0 |
| Disodium EDTA | 0.1 |
| Water (Aqua), demineralized | Ad 100 |
| Total | 100.0 |

Production Method:

Blend all ingredients as listed.

Release Test Procedure:

Non-woven fabric size: 25 cm$^2$

Conc. Emulsion: 5 mg/cm2 (containing 0.5% Phenylethylresorcinol=625 µg/25 cm$^2$)

Conc., wetting liquid: 180 mg/cm2 (4.5 g/25 cm$^2$)

Incubation: 30 min (32° C.)

The required amount of formulation (formula 1-10) was applied homogenous onto a non-woven fabric by using a disposable syringe. The emulsion was dried for 4 h. For each formulation a separate non-woven sheet was used for the test. The non-woven fabric was soaked with the required amount of wetting liquid (formula A) to activate the liberation of the active agent and the fabric is incubated for about 30 min. at about 30° C. to 35° C. Then 2 g of the liquid was squeezed from the non-woven fabric and the amount of actives was determined by HPLC. The results are shown in table 6 and 7.

TABLE 6

HPLC results of the liberation test, formula 1-6

| | Formula | | | | | |
|---|---|---|---|---|---|---|
| | 1 | 2 | 3 | 4 | 5 | 6 |
| Phenylethyl-resorcinol [%] | 3-5 | 0.5-0.7 | 61-65 | 42-46 | 44-48 | 2-3 |

Significant better liberation of phenylethylresorcinol (approx. 20% improved) with emulsion containing 15% maltodextrin (formula 3) in comparison to emulsion without maltodextrin (formula 4). Very poor and no sufficient liberation of phenylethylresorcinol from formula 1, 2 and 6 have been detected, in which no maltodextrin or very high dosages (45%) of maltodextrin was used. An o/w emulsion containing maltodextrin is a very suitable system to improve the liberation of an active ingredient. Therefore another trial was done with an anti-ageing active (formula 7-10).

TABLE 7

HPLC results of the liberation test, formula 7-10

| | Formula | | | |
|---|---|---|---|---|
| | 7 | 8 | 9 | 10 |
| Carnosin [%] | 70-75 | 40-44 | 65-68 | 45-48 |

Improved liberation with 15% maltodextrin (formula 7) in comparison to emulsion without maltodextrin (formula 8).

Example 2

Further Formulation Examples
1=Skin lightening o/w emulsion SPF 24 (UVA/UVB Balance)
2=Lightening balm, SPF 15
3=Refreshing body lotion,
4=Lightening cream o/w
5=Even skin tone emulsion w/o
6=Lightening serum

TABLE 8

| Ingredients | INCI-Name | 1 | 2 | 3 | 4 | 5 | 6 |
|---|---|---|---|---|---|---|---|
| Formulation examples (amounts in 5 w/w) | | | | | | | |
| Skin Lightening Ingredients | | | | | | | |
| SymWhite 377 | Phenylethylresorcinol | 0.5 | | | | 0.3 | |
| Beta-Arbutin | Arbutin | | | | 0.5 | | |
| Sclareolide | Sclareolide | | | | | | 0.3 |
| Nicotinamide | Niacinamide | | | 0.5 | | | |
| Kojic acid | Kojic acid | | 0.5 | | | | |
| Mg ascorbyl phosphate | Magnesium ascorbyl phosphate | | 5.0 | | | 1.0 | |
| Other Ingredients | | | | | | | |
| Abil 350 | Dimethicone | | 2.0 | | | | |
| Actipone ® Laminaria SaccharinaGW | Glycerin, Water (Aqua), Laminaria Saccharina Extract | | | | 1.0 | | |
| Aluminium Stearate | Aluminium Stearate | | | | | 1.2 | |
| Biotive ® L-Arginine | Arginine | 0.5 | 0.6 | 0.9 | | | |
| Carbopol ETD 2050 | Carbomer | | 0.2 | | 0.2 | | |
| Carbopol Ultrez-21 | Acrylates/C10-30 Alkyl Acrylate Crosspolymer | | | | 0.5 | | |
| Corapan TQ | Diethylhexyl 2,6 Naphtalate | | | 3.0 | | | |
| Cutina GMS V | Glyceryl Stearate | | | | 2.0 | | |
| Cutina PES | Pentaerythrityl Distearate | | 2.0 | | | | |
| Dow Corning 246 fluid | Cyclohexasiloxane | 3.0 | | | 1.0 | | |
| Dragosantol 100 | Bisabolol | | 0.2 | | | | |
| Dracorin ® CE | Glyceryl Stearate/Citrate | | | | 3.0 | | |
| Dracorin ® GOC | Glyceryl Oleate Citrate, Caprylic Capric Triglyceride | | | 1.5 | | | |
| Dragoderm ® | Glycerin, Triticum Vulgare (Wheat) Gluten, Water (Aqua) | | | | 2.0 | | |
| Dragosan W/O P | Sorbitan Isostearate, Hydrogenated Castor Oil, Ceresin, Beeswax (Cera Alba) | | | | | 8.0 | |
| Dragosantol ® 100 | Bisabolol | | 0.1 | | | 0.2 | |
| Dragoxat ® 89 | Ethylhexyl Isononanoate | 2.0 | 5.0 | | 4.0 | 7.0 | |
| EDTA B | Tetrasodium EDTA | | | | | | 0.1 |
| EDTA BD | Disodium EDTA | 0.1 | 0.1 | 0.1 | | | |
| Emulsiphos ® | Potassium Cetyl Phosphate, Hydrogenated Palm Glycerides | 2.0 | 2.0 | | | | |
| Ethanol 96% | Ethanol | | | | | 3.0 | |
| Extrapone ® Ginkgo Biloba | Propylene Glycol, Water (Aqua), Ginkgo Biloba Leaf Extract, Glucose, Lactic Acid | | | | 1.0 | | |
| Fragrance | Parfum | 0.2 | 0.3 | 0.2 | 0.4 | 0.3 | 0.1 |
| Frescolat ® MGA | Menthone Glycerin Acetal | | | | | | 0.3 |
| Frescolat ® ML | Menthyl Lactate | | | | 0.2 | | |
| Frescolat ® X-Cool | Menthyl Ethylamido Oxalate | | | 0.5 | | | |
| Glycerine 99.5% | Glycerin | 3.0 | | | 5.0 | 3.0 | |
| Hydrolite ®-5 | Pentylene Glycol | 2.0 | | | 5.0 | | |
| Hydroyiton ®-24 | Water (Aqua), Pentylene Glycol, Glycerin, Lactic Acid, Sodium Lactate, Serine, Urea, Sorbitol, Sodium Chloride, Allantoin | | | | 1.0 | 1.0 | |
| Iso Adipate | Diisopropyl Adipate | | | | 1.0 | | |
| Isodragol ® | Triisononanoin | 2.0 | | | | | |
| Jojoba Oil | Simmondsia Chinensis (Jojoba) Seed Oil | | | | | 2.0 | |
| Keltrol CG RD | Xanthan Gum | 0.4 | 0.2 | 0.2 | 0.1 | | 0.05 |
| Lanette 16 | Cetyl Alcohol | 1 | | | | | |
| Lanette O | Cetearyl Alcohol | 0.5 | | | 3.0 | | |
| Magnesium Sulfate | Magnesium Sulfate | | | | | 0.7 | |
| Maltodextrin | Maltodextrin | 15.0 | 10.0 | 20.0 | 0 | 20.0 | 10.0 |
| Modified Starch | Modified Starch | 5.0 | | 2.0 | | | |
| Dextrine | Dextrine | | | | | | 10.0 |
| Gummi Arabicum | Gummi Arabicum | | | | 25 | | |
| Mannitol | Mannitol | | | | | | 5.0 |
| Neo Heliopan ® 303 | Octocrylene | 10.0 | 4.0 | | | | |
| Neo Heliopan ® 357 | Butylmethoxydibenzoylmethane | 3.0 | 2.0 | 3.0 | | | |
| Neo Heliopan ® E 1000 | Isoamyl p.Methoxycinnamate | 1.0 | | | | | |
| Neo Heliopan ® HMS | Homosalate | 5.0 | | 5.0 | | | |

TABLE 8-continued

Formulation examples (amounts in 5 w/w)

| Ingredients | INCI-Name | 1 | 2 | 3 | 4 | 5 | 6 |
|---|---|---|---|---|---|---|---|
| Neo Heliopan ® Hydro, 20% sol., neutralized with Biotive ® L-Arginine | Aqua, Phenylbenzimidazole Sulphonic Acid, Arginin | 10.0 | 10.0 | 10.0 | | | |
| Neo Heliopan ® OS | Ethylhexyl Salicylate | | 3.0 | 5.0 | | | |
| Neutral Oil | Caprylic/Capric Triglyceride | | | | 6.0 | 8.0 | |
| Ozokerite Wax 2389 | Ozokerite | | | | | 2.0 | |
| PCL-liquid ® 100 | Cetearyl Ethylhexanoate | | 2.0 | | 4.0 | 5.0 | |
| Sodium Hydroxide 10% sol. | Sodium Hydroxide | | | | 0.9 | | |
| Solubilizer | PEG-40 Hydrogenated Castor Oil, Trideceth-9, Propylene Glycol, Water (Aqua) | | | | | | 1.5 |
| SymClariol ® | Decylene Glycol | | 0.1 | | | | |
| SymDiol ® 68 | 1,2 Hexanediol, Caprylyl Glycol | | | | | | 1.0 |
| SymMatrix ® | Maltodextrin, Rubus Fruticosus (Blackberry) Leaf Extract | | | | 0.5 | | |
| SymMollient ® S | Cetearyl Nonanoate | | | 1.0 | 3.0 | | |
| SymMollient ® W/S | Trideceth-9, PEG-5 Isononanoate | | | | | | 2.0 |
| SymSave ® H | Hydroxyacetophenone | 0.8 | | | 0.5 | | |
| Tegosoft TN | C12-15 Alkyl Benzoate | | | 5.0 | | | |
| Vitamin E acetat | Tocopherol Acetate | 0.5 | 0.5 | 0.5 | | 0.2 | |
| Water, demin. | Water (Aqua) | ad100 | ad100 | ad100 | ad100 | ad100 | ad100 |

Example 3

Further Formulation Examples
1=Anti aging & deep hydration balm
2=Self tan lotion o/=
3=Skin soothing emulsion o/w for sensitive skin
4=Anti wrinkle emulsion w/o
5=Anti Cellulite emulsion o/w
6=Anti acne emulsion o/w

TABLE 9

Formulation examples

| Ingredients | INCI-Name | 1 | 2 | 3 | 4 | 5 | 6 |
|---|---|---|---|---|---|---|---|
| Active Ingredient | | | | | | | |
| Abil 350 | Dimethicone | | 0.5 | | | | |
| Actipone ® Nutgrasass Root GW | Water (Aqua), Glycerin, Cyperus Rotundus Root Extract | 1.0 | | | | | |
| Aloe Vera Gel Conc. 10:1 | Aloe Barbadensis Leaf Juice | 1.0 | | | | | 1.0 |
| Aluminium Stearate | Aluminium Stearate | | | | 1.2 | | |
| Avicel PC 591 | Microcrystalline Cellulose, Cellulose Gum | | 0.5 | | | | |
| Beeswax | Beeswax | | | | 2.0 | | |
| Biotive ® L-Arginine | Arginine | 0.5 | | | | | |
| Biotive ® Troxerutin | Troxerutin | 0.5 | | | | | |
| Carbopol ETD 2050 | Carbomer | | | 0.2 | | | 0.2 |
| Coffein pure | Coffein | | | | | 2.0 | |
| Corapan TQ | Diethylhexyl 2,6 Naphtalate | | | | | | |
| Cosmedia SP | Sodium Polyacrylates | | | | | 1.0 | |
| Cutina GMS V | Glyceryl Stearate | | | 2.0 | | | 2.0 |
| Cutina PES | Pentaerythrityl Distearate | | | | | | |
| Dermacryl AQF | Acrylates Copolymer | 2.0 | | | | | |
| Dihydroxyaceton | Dihydroxyaceton | | 5.0 | | | | |
| Dipropylene Glycol | Dipropylene Glycol | | | | | | |
| Dow Corning 193 surfactant | PEG-12 Dimethicone | | | | | | |
| Dow Corning 246 fluid | Cyclohexasiloxane | 3.0 | 1.0 | | | | |
| D-Panthenol 75 L | Panthenol | | | | 0.5 | | 0.5 |
| Dracorin ® CE | Glyceryl Stearate/Citrate | | | 3.0 | | | 2.5 |
| Dracorin ® GOC | Glyceryl Oleate Citrate, Caprylic Capric Triglyceride | | | | | 0.4 | |

TABLE 9-continued

Formulation examples

| Ingredients | INCI-Name | 1 | 2 | 3 | 4 | 5 | 6 |
|---|---|---|---|---|---|---|---|
| DragoCalm ® | Water, Glycerin, Avena Sativa (Oat Kernel Extract) | | | | 1.0 | | |
| Dragoderm ® | Glycerin, Triticum Vulgare (Wheat) Gluten, Water (Aqua) | | | 2.0 | | | |
| Dragosan W/O P | Sorbitan Isostearate, Hydrogenated Castor Oil, Ceresin, Beeswax (Cera Alba) | | | | 8.0 | | |
| Dragosantol ® 100 | Bisabolol | | 0.1 | | 0.2 | | |
| Dragosine ® | Carnosine | | | | 0.1 | | |
| Dragoxat ® 89 | Ethylhexyl Isononanoate | 2.0 | 3.0 | 4.0 | 7.0 | 4.0 | 4.0 |
| EDTA BD | Disodium EDTA | 0.1 | 0.1 | | | | |
| Emulsiphos ® | Potassium Cetyl Phosphate, Hydrogenated Palm Glycerides | 2.0 | 2.0 | | | | |
| Ethanol 99.7% | Ethanol | | | | | 15.0 | 10.0 |
| Fragrance | Parfum | 0.2 | 0.5 | 0.4 | 0.3 | 0.5 | 0.3 |
| Frescolat ® MGA | Menthone Glycerin Acetal | 0.5 | | | | | |
| Frescolat ® ML | Menthyl Lactate | | 1.0 | | | | |
| Frescolat ® X-Cool | | | | | | 0.5 | |
| Glycerin 99.5% | Glycerin | 3.0 | 2.0 | 5.0 | 3.0 | | |
| Hydrolite ®-5 | Pentylene Glycol | 2.0 | 5.0 | | | | |
| Hydroyiton ®-24 | Water, Pentylene Glycol, Glycerin, Lactic Acid, Sodium Lactate, Serine, Urea, Sorbitol, Sodium Chloride, Allantoin | | | | 1.0 | 1.0 | |
| Hydroyiton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | 4.0 | | | | | 2.0 |
| Iso Adipat | Diisopropyl Adipate | 3.0 | | | | | 2.0 |
| Isodragol ® | Triisononanoin | 2.0 | | | | | |
| Jojoba Oil | Simmondsia Chinensis (Jojoba) Seed Oil | | | | 2.0 | | |
| Keltrol CG RD | Xanthan Gum | 0.4 | 0.25 | 0.1 | | | |
| Lactic Acid 90% | Lactic Acid | | | 0.09 | | | |
| Lanette 16 | Cetyl Alcohol | 1.0 | | | | | |
| Lanette O | Cetearyl Alcohol | 0.5 | 1.4 | 3.0 | | | |
| Lara Care A-200 | Galactoarabinan | 0.3 | | | | | |
| Magnesium Sulfate | Magnesium Sulfate | | | | 0.7 | | |
| Maltodextrin | Maltodextrin | | | 15.0 | 5.0 | 5.0 | |
| Modified Starch | Modified Starch | | | | 5.0 | | 5.0 |
| Dextrine | Dextrine | 10.0 | | | | | |
| Gummi Arabicum | Gummi Arabicum | | | | 5.0 | | |
| Mannitol | Mannitol | | | | | | 10.0 |
| Mineral Oil | Mineral Oil | | | | 8.0 | | |
| Neo Heliopan ® 303 | Octocrylene | | 8.0 | | | | |
| Neo Heliopan ® 357 | Butylmethoxydibenzoylmethane | | 1.5 | | | | |
| Neutral Oil | Caprylic/Capric Triglyceride | 10.0 | | 6.0 | | 5.0 | |
| PCL-liquid ® 100 | Cetearyl Ethylhexanoate | | 2.0 | 4.0 | 5.0 | | |
| PCL-Solid ® | Stearyl Heptanoate, Stearyl Caprylate | | 1.0 | 3.0 | | | |
| Retinol, 10% | Retinol | | | | 0.1 | | |
| Sheabutter | Butyrospermum Parkii (Shea) Butter | | | 2.0 | 3.0 | | |
| Sodium Hydroxide 10% sol. | Sodium Hydroxide | | | | 0.9 | | |
| Sym3D ® | Hydroxymethoxyphenyl Propylmethylmethoxybenzofuran | | | | 0.25 | | |
| SymCalmin ® | Pentylene Glycol, Butylene Glycol, Hydroxyphenyl Propamidobenzoic Acid | | | | 1.0 | | |
| SymDiol ® 68 | 1,2 Hexanediol, Caprylyl Glycol | | | | 0.5 | 0.3 | 0.5 |
| SymFit ® 1617 | Trimethylcyclohexyl Butylcarbamate | | | | | 0.2 | |
| SymGlucan ® | Water (Aqua) Glycerin, Beta Glucan | 2.0 | | | 1.0 | | |
| SymHelios ® 1031 | Benzylidene Dimethoxydimethylindanone | 0.1 | | | | | |
| SymMatrix ® | Maltodextrin, Rubus Fruticosus (Blackberry) Leaf Extract | | | | 0.5 | | |

TABLE 9-continued

Formulation examples

| Ingredients | INCI-Name | 1 | 2 | 3 | 4 | 5 | 6 |
|---|---|---|---|---|---|---|---|
| SymMollient ® S | Cetearyl Nonanoate | 2.0 | | | | | |
| SymMollient ® W/S | Trideceth-9, PEG-5 Isononanoate | | | | | | 1.0 |
| SymRelief ® | Bisabolol, Zingiber Officinale (Ginger) Root Extract | 0.1 | | 0.2 | | | |
| SymRepair ® 100 | Hexyldecanol, Bisabolol, Cetylhydroxyproline Palmitamide, Stearic Acid, Brassica Campestris (Rapeseed Sterols) | | | | 3.0 | | |
| SymSave ® H | Hydroxyacetophenone | 0.8 | | 0.5 | 0.8 | 0.5 | 0.5 |
| SymSitive ® 1609 | Pentylene Glycol, 4-t-Butylcyclohexanol | | | 3.0 | | | |
| SymVital ® Age Repair | Zingiber Officinale (Ginger) Root Extract | | | | 0.2 | | |
| Tapioca Pure | Tapioca Starch | 5.0 | | | | | |
| Vitamin E acetat | Tocopherol Acetate | 0.5 | | | 0.2 | 0.5 | |
| Water, demin. | Water (Aqua) | ad100 | ad100 | ad100 | ad100 | ad100 | ad100 |

Example 4

Further Formulation Examples: Wetting Liquids
1=Moisturizing wetting liquid
2=Calming wetting liquid
3=Wetting liquid for sensitive skin
4=Refreshing wetting liquid
5=Anti Acne wetting liquid
6=Warming anti cellulite wetting liquid
7=Anti-ageing wetting liquid
8=Wetting liquid for w/o systems

TABLE 10

Wetting liquids

| Ingredients | INCI-Name | 1 | 2 | 3 | 4 | 5 | 6 | 7 | 8 |
|---|---|---|---|---|---|---|---|---|---|
| Azelaic Acid | Azelaic Acid | | | | | 10.0 | | | |
| Benzoylperoxid | Benzoylperoxid | | | | | 1.0 | | | |
| Coffein | Coffein | | | | | | 0.5 | | |
| Dragoderm ® | Dragoderm | | | | | | | 5.0 | |
| Dragosine ® | Carnosine | | | | | | | 0.3 | |
| EDTA BD | Disodium EDTA | | 0.1 | 0.1 | 0.1 | 0.1 | 0.1 | | |
| Ethanol | Ethanol | | | | 5.0 | 5.0 | | | 10.0 |
| Farnesol | Farnesol | | | | | 0.1 | | | |
| Fragrance | Fragrance | 0.05 | 0.1 | 0.2 | 0.2 | 0.1 | 0.1 | 0.1 | |
| Frescolat ® X-Cool | Menthyl Ethylamido Oxalate | | | | 0.5 | | | | |
| Glycerin | Glycerin, 86.5% | 30.0 | 10.0 | 4.0 | 4.0 | 4.0 | 20.0 | 30.0 | |
| Hydrolite ®-5 | Pentylene Glycol | 5.0 | 5.0 | 3.0 | 3.0 | 3.0 | 5.0 | 5.0 | 20.0 |
| Hydroyiton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | 5.0 | | 1.0 | 1.0 | | | | |
| Isoadipate ® | Diisopropyl Adipate | | | | | | | | 70.0 |
| SymCalmin ® | Pentylene Glycol, Butylene Glycol, Hydroxyphenyl Propamidobenzoic Acid | | 2.0 | | | | | | |
| SymDiol ® 68 | 1,2 Hexanediol, Caprylyl Glycol | | | 1.0 | 0.5 | 0.5 | 0.5 | | |
| SymGlucan ® | Water (Aqua) Glycerin, Beta Glucan | | | | | | | 3.0 | |
| SymMollient ® W/S | Trideceth-9, PEG-5 Isononanoate | | | | 1.0 | | | | |
| SymRelief ® | Bisabolol, Zingiber Officinale (Ginger) Root Extract | | | | 0.1 | 0.1 | 0.1 | | |
| SymSave ® H | Hydroxyacetophenone | | | | 0.5 | 0.5 | 0.5 | 0.5 | |
| SymSitive ® 1609 | Pentylene Glycol, 4-t-Butylcyclohexanol | | | 3.0 | | | | | |
| Vanillyl Butyl Ether | Vanillyl Butyl Ether | | | | | | 0.3 | 0.3 | |
| Water, demin. | Water (Aqua) | ad 100 | ad 100 | ad 100 | ad 100 | ad 100 | ad 100 | ad 100 | ad 100 |

Example 5

Skin Feel Test

To determine the greasy skin feel, ten test persons have been asked to evaluate a two component face mask (non-woven, printed with formula 3 and activated with wetting liquid, formula A) in comparison to a "ready to use" standard market sample. On a scale from 1-10 the test persons were asked about the grade of greasy/discomfort skin feel. The test results are shown in table 6.

TABLE 11

Test results about the skin feel

| Test person | Fase mask comprising formula 3 | Standard "ready to use" face mask |
|---|---|---|
| 1 | 3 | 4 |
| 2 | 4 | 8 |
| 3 | 4 | 8 |
| 4 | 6 | 6 |
| 5 | 3 | 6 |
| 6 | 1 | 4 |
| 7 | 4 | 8 |
| 8 | 3 | 3 |
| 9 | 7 | 9 |
| 10 | 2 | 4 |

8 of 10 subjects estimated a significant less greasy/discomfort skin feel for face mask of the present invention (non-woven fabric, printed with formula 3 and activated with wetting liquid, formula A) in comparison to a "ready to use" standard market sample.

The invention claimed is:

1. A delivery system, comprising
   (i) a basic body,
   (ii) an active-substance preparation, and
   (iii) a separate wetting liquid,
   wherein
   (i) the basic body comprises a non-woven fibrous material,
   (ii) the active-substance preparation is an o/w emulsion which is printed onto the basic body (i),
   (iii) the wetting liquid comprises water and at least one active other than water to start liberation of an active agent of the active-substance preparation,
   said active agent is selected from (a) whitening or brightening agents and (b) carriers, and
   the active other than water is selected from the group consisting of azelaic acid, benzoylperoxide, coffein, carnosine, farnesol, menthyl ethylamido oxalate, allantoin, sodium hyaluronate, diisopropyl adipate, 1,2-hexanediol, caprylyl glycol, beta-glucan, trideceth-9, PEG-5 isononanoate, bisabolol, zingiber officinale root extract, hydroxyacetophenone, urea, vanillyl butyl ether, and mixtures thereof.

2. The system of claim 1, wherein the fibrous material is selected from the group consisting of natural and synthetic fibrous material and mixtures thereof.

3. The system of claim 1, wherein the o/w active-substance preparation emulsion comprises at least one polysaccharide as carrier material.

4. The system of claim 3, wherein the polysaccharide is selected from the group consisting of maltodextrin, modified starch, dextrin, gummi arabicum, mannitol and mixtures thereof.

5. The system of claim 1, wherein the o/w active-substance preparation emulsion comprises
   (a) from 0.001 w.t. % to 70 w.t. % of at least one active agent, and
   (b) from 5 w.t. % to 50 w.t. %, of a carrier material, each based on the total amount of the active-substance preparation.

6. The system of claim 1, wherein the delivery system is a face mask or facial sheet mask or a cosmetical or pharmaceutical care system for skin that is useful as a treatment for upper legs and arms, arm pits, breast or back.

7. The system of claim 1, wherein the basic body comprises at least one layer of fibrous material.

8. A sheet-like cosmetic delivery system according to claim 6, which is obtained by printing a non-woven fibrous material with the o/w emulsion of the active-substance preparation, and
   separately preparing the wetting liquid.

9. The system of claim 1, wherein the active agent of the active-substance preparation to be released is a whitening or brightening agent selected from the group consisting of diphenylmethanes, macrocyclic compounds, botanical extracts that contain components that inhibit melanin production in skin, sclareolide, *Tetraselmis Suecica* extract, licorice extract, pomegranate extract, hinokitiol, protocatechuic acid, *Ferula Foetida* extract, resveratrol, oxyresveratrol, resveratrol phosphate, resveratrol ferulate, ferulic acid, ferulic acid phosphate, viniferol, Saxifrage extract, Grape extract, mulberry extract, *Scutelleria* Root extract, cucumber extract, apple extract, Scutelleria extract, green tea extract, butylene glycol/water/*Denothera Biennis* seed extract, evening primrose extract, fatty acid esters of ascorbic acid, ascorbyl palmitate, *Euphrasia Officianalis* extract, kinetin, ascorbyl glucoside, grape seed extract, vineferol, pomegranate extract, tetrahydrocurcumins, *Acmella Oleracea* extract, Aloesin, field dock extract, *aspergillus* ferment extract, molasses extract, 4-(1-Phenylethyl) 1-,3 benzenediol, and mixtures thereof.

10. A method for preparing the system claim 8, comprising the steps of
    printing the o/w active-substance preparation emulsion onto non-woven fibrous material and
    separately preparing the wetting liquid.

11. The method of claim 10, wherein the active agent of the active-substance preparation to be released is a whitening or brightening agent selected from the group consisting of diphenylmethanes, macrocyclic compounds, botanical extracts that contain components that inhibit melanin production in skin, sclareolide, *Tetraselmis Suecica* extract, licorice extract, pomegranate extract, hinokitiol, protocatechuic acid, *Ferula Foetida* extract, resveratrol, oxyresveratrol, resveratrol phosphate, resveratrol ferulate, ferulic acid, ferulic acid phosphate, viniferol, Saxifrage extract, Grape extract, mulberry extract, *Scutelleria* Root extract, cucumber extract, apple extract, Scutellaria extract, green tea extract, butylene glycol/water/*Denothera Biennis* seed extract, evening primrose extract, fatty acid esters of ascorbic acid, ascorbyl palmitate, Euphrasia Officianalis extract, kinetin, ascorbyl glucoside, grape seed extract, vineferol, pomegranate extract, tetrahydrocurcumins, *Acmella Oleracea* extract, Aloesin, field dock extract, aspergillus ferment extract, molasses extract, 4-(1-Phenylethyl) 1-,3 benzenediol, and mixtures thereof.

12. The method of claim 10, wherein the active agent of the active-substance preparation to be released further comprises is an anti-ageing active selected from the group consisting of antioxidants, matrix-metalloproteinase inhibitors, skin moisturizing agents, glycosaminoglycan stimulators, anti-inflammatory agents, TRPV1 antagonists and plant extracts and mixtures thereof.

13. A method of delivering an active agent to skin with the system of claim 1, comprising the steps of:
  (i) providing the basic body that comprises the non-woven fibrous material on which the active-substance preparation is printed,
  (ii) bringing the basic body resulting from step (i) in contact with the wetting liquid, which comprises said at least one active to start the release of the active agent of the active-substance preparation, to release the active agent to the skin part which is to be treated, and
  (iii) bringing the wetted basic body into contact with the skin.

14. The system of claim 1, wherein the carrier is a polysaccharide.

15. The system of claim 14, wherein the polysaccharide is maltodextrin.

\* \* \* \* \*